US006804550B1

(12) United States Patent
Murray

(10) Patent No.: US 6,804,550 B1
(45) Date of Patent: Oct. 12, 2004

(54) METHOD AND APPARATUS FOR FRANK LEAD RECONSTRUCTION FROM DERIVED CHEST LEADS

(75) Inventor: William J. Murray, Wakefield, MA (US)

(73) Assignee: Draeger Medical Systems, Inc., Danvers, MA (US)

( * ) Notice: Subject to any disclaimer, the term of this patent is extended or adjusted under 35 U.S.C. 154(b) by 185 days.

(21) Appl. No.: 09/671,532

(22) Filed: Sep. 27, 2000

Related U.S. Application Data

(60) Provisional application No. 60/156,606, filed on Sep. 29, 1999.

(51) Int. Cl.[7] .................................................. A61B 5/04
(52) U.S. Cl. ....................................... 600/509; 600/512
(58) Field of Search ......................... 600/300, 508–528

(56) References Cited

U.S. PATENT DOCUMENTS

| | | | | |
|---|---|---|---|---|
| 4,216,780 A | * | 8/1980 | Rubel et al. ................ | 600/512 |
| 4,292,977 A | * | 10/1981 | Krause et al. .............. | 600/525 |
| 4,697,597 A | * | 10/1987 | Sanz et al. .................. | 600/512 |
| 6,052,615 A | * | 4/2000 | Feild et al. .................. | 600/509 |
| 6,358,214 B1 | * | 3/2002 | Tereschouk ................. | 600/508 |
| 6,496,720 B1 | * | 12/2002 | Feild ........................... | 600/509 |

OTHER PUBLICATIONS

MacFarlane et al, Comprehensive Electrocardiography, vol. 1, Chapter 11, "Lead Systems" Pergamon Press, 1989, pp. 315–352.

* cited by examiner

*Primary Examiner*—George R. Evanisko
(74) *Attorney, Agent, or Firm*—Jack Schwartz & Assoc.

(57) ABSTRACT

In an ECG monitoring and analyzing system of the type where electrodes are placed on a subject for detecting electrical activity of a heart, and where the electrode placement is such that Frank Leads X, Y and Z can be constructed from the detected electrical activity, an ECG signal transformation network for providing Frank X, Y and Z leads, comprises an input, responsive to a set of input signals corresponding to no more than derived chest leads dV1, dV2, dV3, dV4, dV5 and dV6, a memory for storing coefficients of a transformation matrix, and an output, for providing transformation matrix output signals corresponding to application of said transformation matrix coefficients to said input signals, said output signals corresponding to said Frank X, Y and Z leads. The invention reduces bandwidth requirements in an ECG signal communication network, as well as the complexity of the processing required for constructing the Frank Leads.

13 Claims, 4 Drawing Sheets

TABLE 1 SMS PRIME LEAD TO X, Y, Z TRANSFORMATION

|   | V1 | V2 | V3 | V4 | V5 | V6 | III | II | I |
|---|---|---|---|---|---|---|---|---|---|
| X | -0.781 | 0.000 | 0.171 | 0.610 | 0.000 | 0.000 | 0.000 | 0.000 | 0.000 |
| Y | 0.000 | 0.000 | 0.000 | 0.000 | 0.345 | -1.000 | 0.000 | 0.437 | -0.218 |
| Z | -0.264 | -0.374 | -0.231 | 0.133 | -0.736 | 0.000 | 0.000 | 0.000 | 0.000 |

TABLE 2 REDUCED DOWER TRANSFORMATION

|   | X | Y | Z |
|---|---|---|---|
| dV1 | -0.515 | 0.157 | -0.917 |
| dV2 | 0.044 | 0.164 | -1.387 |
| dV3 | 0.882 | 0.098 | -1.277 |
| dV4 | 1.213 | 0.127 | -0.601 |
| dV5 | 1.125 | 0.127 | -0.086 |
| dV6 | 0.831 | 0.076 | 0.230 |
| dIII | -0.397 | 1.301 | -0.191 |
| dII | 0.235 | 1.066 | -0.132 |
| dI | 0.632 | -0.235 | 0.059 |

TABLE 3 EDENBRANDT TRANSFORMATION - 8 LEADS TO X, Y, Z

|   | dV1 | dV2 | dV3 | dV4 | dV5 | dV6 | dII | dI |
|---|---|---|---|---|---|---|---|---|
| X | -0.172 | -0.074 | 0.122 | 0.231 | 0.239 | 0.194 | -0.010 | 0.156 |
| Y | 0.057 | -0.019 | -0.106 | -0.022 | 0.041 | 0.048 | 0.887 | -0.227 |
| Z | -0.229 | -0.310 | -0.246 | -0.063 | 0.055 | 0.108 | 0.102 | 0.022 |

FIG. 2
PRIOR ART

TABLE 4 SMS PRIME LEAD TO X, Y, Z TRANSFORMATION

|   | V1     | V2     | V3     | V4    | V5    | V6     | III   | II    | I      |
|---|--------|--------|--------|-------|-------|--------|-------|-------|--------|
| X | -0.781 | 0.000  | 0.171  | 0.610 | 0.000 | 0.000  | 0.000 | 0.000 | 0.000  |
| Y | 0.000  | 0.000  | 0.000  | 0.000 | 0.345 | -1.000 | 0.000 | 0.437 | -0.218 |
| Z | -0.264 | -0.374 | -0.231 | 0.133 | 0.736 | 0.000  | 0.000 | 0.000 | 0.000  |

TABLE 5 REDUCED DOWER TRANSFORMATION

|       | X      | Y      | Z      |
|-------|--------|--------|--------|
| dV1   | -0.515 | 0.157  | -0.917 |
| dV2   | 0.044  | 0.164  | -1.387 |
| dV3   | 0.882  | 0.098  | -1.277 |
| dV4   | 1.213  | 0.127  | -0.601 |
| dV5   | 1.125  | 0.127  | -0.086 |
| dV6   | 0.831  | 0.076  | 0.230  |
| dIII  | -0.397 | 1.301  | -0.191 |
| dII   | 0.235  | 1.066  | -0.132 |
| dI    | 0.632  | -0.235 | 0.059  |

TABLE 6 MURRAY TRANSFORMATION - 6 LEADS TO X, Y, Z

|   | dV1 | dV2 | dV3 | dV4 | dV5 | dV6 |
|---|---|---|---|---|---|---|
| X | -0.40757884750469 | -0.13051998992585 | 0.32261160169867 | 0.25098541170428 | 0.12385117804856 | 0.08124965185519 |
| Y | 4.18733133624375 | 0.88597070838058 | -3.71987635614205 | 0.07914411954946 | 2.77239067806103 | 2.62753615316718 |
| Z | 0.18775335982562 | -0.22034870637739 | -0.61208118838009 | -0.04513634534679 | 0.34281776711603 | 0.37945166118190 |

METHOD AND APPARATUS FOR FRANK LEAD RECONSTRUCTION FROM DERIVED CHEST LEADS

CROSS-REFERENCE TO RELATED APPLICATIONS

This application claims priority from U.S. Provisional Application Ser. No. 60/156,606 filed Sep. 29, 1999.

BACKGROUND OF THE INVENTION

1. Field of the Invention

The present invention relates to electrophysiology, and more particularly to an ECG monitoring and analyzing system for providing Frank X, Y and Z lead signals representative of electrical activity of a human heart using a reduced set of derived chest leads.

2. Brief Description of the Prior Art

Over the last sixty years, a variety of diagnostic procedures have been developed for sensing and analyzing the electrical activity of the human heart. These include: (a) electrocardiography, (b) vectorcardiography and (c) polarcardiography, all of which depend upon related apparatus used to produce records derived from voltages produced by the heart which are detected by electrodes placed on the surface of the subject's body.

The records so produced are graphical in character and require interpretation and analysis to relate the resulting information to the heart condition of the patient or other subject. Historically, such records have been produced directly as visible graphic recordings from wired connections extending from the subject to the recording device. With advances in computer technology, it has become possible to produce such records in the form of digitally stored information for later replication of retrieval and analysis. Likewise, with advances in communication technology, not only has wireless sensing become possible, but also remote replication, retrieval and analysis of the acquired signals.

(a) Electrocardiography

The production of a conventional 12-lead electrocardiogram (ECG) involves the placement of 10 lead electrodes (one of which is a ground or reference electrode) at selected points on the surface of a subject's body. Each electrode acts in combination with one or more other electrodes to detect voltages produced by depolarization and repolarization of individual heart muscle cells. The detected voltages are combined and processed to produce 12 tracings of time varying voltages. The tracings so produced are as follows:

| Lead | Voltage | Lead | Voltage |
|---|---|---|---|
| I | $vL - vR$ | V1 | $v1 - (vR + vL + vF)/3$ |
| II | $vF - vR$ | V2 | $v2 - (vR + vL + vF)/3$ |
| III | $vF - vL$ | V3 | $v3 - (vR + vL + vF)/3$ |
| aVR | $vR - (vL + vF)/2$ | V4 | $v4 - (vR + vL + vF)/3$ |
| aVL | $vL - (vR + vF)/2$ | V5 | $v5 - (vR + vL + vF)/3$ |
| aVF | $vF - (vL + vR)/2$ | V6 | $v6 - (vR + vL + vF)/3$ | where, in the standard, most widely used system for making short term electrocardiographic recordings of supine subjects, the potentials indicated above, and their associated electrode positions, are:

vL potential of an electrode on the left arm;

vR potential of an electrode on the right arm;

vF potential of an electrode on the left leg;

v1 potential of an electrode on the front chest, right of sternum in the 4th rib interspace;

v2 potential of an electrode on the front chest, left of sternum in the 4th rib interspace;

v4 potential of an electrode at the left mid-clavicular line in the 5th rib interspace;

v3 potential of an electrode midway between the v2 and v4 electrodes;

v6 potential of an electrode at the left mid-axillary line in the 5th rib interspace;

v5 potential of an electrode midway between the v4 and v6 electrodes;

vG (not indicated above) is a ground or reference potential with respect to which potentials vL, vR, vF, and v1 through v6 are measured. Typically, though not necessarily, the ground or reference electrode is positioned on the right leg.

Correct interpretation of an ECG requires a great deal of experience since it involves familiarity with a wide range of patterns in the tracings of the various leads. Any ECG which uses an unconventional system of leads necessarily detracts from the body of experience that has been developed, in the interpretations of conventional ECGs, and may therefore be considered generally undesirable. The recorded signals would be understandable only by a relative few who were familiar with the unconventional system.

Nevertheless, other lead systems have evolved from improvements in instrumentation that have permitted extension of electrocardiography to ambulatory, and even vigorously exercising subjects—and to recordings made over hours, or even days. For example, in stress testing the electrodes are moved from the arms to the torso, although the same number of electrodes (10) are used. The tracings I, II, III, aVR, aVL and aVF are altered by this modification.

(b) Vectorcardiography

The pattern of potential differences on a body surface resulting from electrical activity of the heart can be mathematically approximated by replacing the heart with a dipole equivalent cardiac generator. The magnitude and orientation of this dipole are represented by the heart vector which is continually changing throughout the cycle of the heart beat. The XYZ coordinates of the heart give rise to time varying x, y and z signals, which may be written out as x, y and z tracings. Orthogonal leads to give these tracings were developed by Ernest Frank (see An Accurate, Clinically Practical System For Spatial Vectorcardiography, Circulation 13: 737, May 1956). Frank experimentally determined the image surface for one individual, and from this proposed a system using seven electrodes on the body, plus a grounding electrode. The conventional letter designations for such electrodes, and their respective positions were:

E at the front midline;

M at the back midline;

I at the right mid-axillary line;

A at the left mid-axillary line;

C at a 45.degree. angle between the front midline and the left mid-axillary line;

F on the left leg; and

H on the back of the neck.

The first five electrodes (E, M, I, A and C) were all located at the same transverse level—approximately at the fourth of the fifth rib interspace. A linear combining network of resistors attached to these electrodes gave suitably scaled x, y and z voltage signals as outputs.

Unfortunately, x, y and z tracings are not as easy to interpret as 12 lead ECGs. However, Frank intended his system for a different purpose: vectorcardiography.

Although it has long formed a basis for teaching electrocardiography, vectorcardiography has never become widely used. The technique was demanding and the system of electrode placement was different from that required for conventional ECG's. Extra work was required, and it would still be necessary to record a 12-lead ECG separately with a different placement of electrodes.

(c) Polarcardiography

An alternative representation of the heart vector, known as polarcardiography, has been exploited since the early 1960's (see G. E. Dower, Polarcardiography, Springfield, Ill., Thomas, 1971). It has certain inherent advantages in defining abnormalities, and forms the basis of a successful program for automated analysis. Based on the x, y and z signals, polarcardiography employs the Frank lead system. In order to render it competitive with the established 12-lead ECG, the lead vector concept has been employed to derive a resistor network that would linearly transform the x, y and z signals into analogs of the 12-lead ECG signals called herein "derived 12-lead signals" (see G. E Dower, A Lead Synthesizer for the Frank Lead System to Simulate the Standard 12-Lead Electrocardiogram, J. Electrocardiol 1: 101, 1968, G. E. Dower, H. B. Machado, J. A. Osborne, On Deriving the Electrocardiogram From Vectorcardiographic Leads, Clin Cardiol 3: 97, 1980; and G. E. Dower, The ECGD: A Derivation of the ECG from VCG leads (ecitorial), J. Electrocardiol 17: 189,1984). The derived 12-lead ECG is commonly referred to as the ECGD. Because the ECGD can be acceptable to an interpreting physician, it is not necessary for the technician to apply all the electrodes required for a conventional ECG. Further, associated computer facilities can make vectorcardiograms and other useful displays available from the x, y and z recordings. Nevertheless, the number of electrodes called for by the Frank lead system are required. In addition, the effort required by the technician recording the x, y and z signals is about the same as for a conventional ECG.

FIG. 1 illustrates a prior art patient monitoring system, such as manufactured and sold by Siemens Medical Systems, Inc. of Iselin, N.J., using the SC7000 Bedside Monitor 1, an Infinity Communication Network 2, and a MultiView Workstation (MVWS 3). As shown therein, limb lead electrodes RA, LA, RL, and LL are placed on a patient in the standard limb electrode positions. Chest electrodes V1, V2, V3, V4, V5, and V6 are placed on the patient in Frank electrode positions I, E, C, A, M, and H respectively. The contribution of the Frank electrode F is computed algebraically from the formula F=((2×lead II)−(lead I))/3.

The following linear equations represent the SMS-Prime lead to X, Y, Z transformation processing step 5, carried out in Bedside Monitor 1:

$$X = 0.610*V4 + 0.171*V3 - 0.781*V1 \quad (EQ\ 1)$$

$$Y = 0.437*II - 0.218*I + 0.345*V5 - 1.000*V6 \quad (EQ\ 2)$$

$$Z = 0.133*V4 + 0.736*V5 - 0.264*V1 - 0.374*V2 - 0.231*V3 \quad (EQ\ 3)$$

In FIG. 2, TABLE 1 is a matrix representation of the above equations.

The X, Y, and Z leads computed using the SMS Prime Lead to X, Y, Z Transformation are transformed in Monitor 1 using a reduced Dower Transformation processing step 6 outlined in TABLE 2 of FIG. 2. These two linear transformations combine to generate a set of derived leads in the bedside monitor 1 that are made available on the Communication Network 2. The set of derived leads available on Network 2 consists of derived(d) leads dI, dII, dIII, dV1, dV2, dV3, dV4, dV5, and dV6. An algebraic formula is used to derive the augmented leads locally on Monitor 1 in processing step 7 as shown below.

$$aVR = -0.5(I+II)$$

$$aVR = I - 0.5\ (II)$$

$$aVF = II - 0.5(I)$$

Given that L is a 9×1 lead array representing lead values at a particular instant, $$L = \begin{bmatrix} V1 \\ V2 \\ V3 \\ V4 \\ V5 \\ V6 \\ III \\ II \\ I \end{bmatrix}$$

and that SMSPrime represents the 3×9 transformation in TABLE 1, and RDower1 represents the 9×3 transformation in TABLE 2, the derived lead set D(dI, dII, dIII, dV1, dV2, dV3, dV4, dV5, and dV6) can be computed as follows:

$$D = R\text{Dower} \cdot SMS\text{Prime} \cdot L$$

The MVWS 3 is located at a remote location, such as at a nurses station, and receives the as input signals the output signals put on the Communication Network 2 from the Bedside Monitor 1. A software application within MVWS 3 consumes the set of derived leads available on the Network 2 and reconstructs the X, Y, Z leads using the Edenbrandt transformation represented in TABLE 3 of FIG. 2.

Given that N is an 8×1 lead array representing derived lead values at a particular instant, $$N = \begin{bmatrix} dV1 \\ dV2 \\ dV3 \\ dV4 \\ dV5 \\ dV6 \\ dII \\ dI \end{bmatrix}$$

and that Edenbrandt represents the 3×8 transformation in TABLE 3, the derived Frank lead set F(X, Y, Z) can be computed as follows:

$$F = \text{Edenbrandt} \cdot N$$

The same algebraic formulas which were used to derive the augmented leads on Monitor 1 is used to derive the augmented leads locally on the MVWS 3. These are actually derived augmented leads, since the input to the equations are in fact derived leads dI and dII.

Clinicians have expressed a preference for sampled (i.e., actual) limb leads over the derived limb leads in such an ECG application. Unfortunately, the prior work does not provide for the use of sampled limb leads. If sampled limb leads are substituted for the derived dI and dII, the reconstruction of the Frank X, Y, Z lead using the Edenbrandt transformation outlined in TABLE 3 fails.

Accordingly, there remains a need for an improved method and apparatus for developing Frank x, y and z signals for analyzing activity of the human heart, and which uses a reduced number of derived signals. The present invention fulfills these needs and provides other related advantages. More specifically, the present invention reduces bandwidth requirements in the signal transmission network, as well as the number of CPU cycles required to reconstruct the Frank Lead(s) X, Y, and Z (signals dI and dII are no longer needed, as well as the calculations according for these signals, compare Table 3 to Table 6). It also allows the actually sampled limb leads to be maintained throughout the system, rather than derived limb leads.

SUMMARY OF THE INVENTION

In an ECG monitoring and analyzing system of the type where electrodes are placed on a subject for detecting electrical activity of a heart, and where the electrode placement is such that Frank Leads X, Y and Z can be constructed from the detected electrical activity, a method and apparatus for ECG signal transformation to Frank X, Y and Z leads, comprises an input, responsive to a set of input signals corresponding to no more than derived chest leads dV1, dV2, dV3, dV4, dV5 and dV6, a memory for storing coefficients of a transformation matrix, and an output, for providing transformation matrix output signals corresponding to application of said transformation matrix coefficients to said input signals, said output signals corresponding to said Frank X, Y and Z leads.

The invention reduces bandwidth requirements in a ECG signal communication network, as well as the complexity of the processing required for constructing the Frank Leads. Other features and advantages of the present invention will also become apparent from the following more detailed description, taken in conjunction with the accompanying drawings which illustrate, by way of a preferred example, the principles of the invention.

BRIEF DESCRIPTION OF THE DRAWINGS

The accompanying drawings illustrate the invention. In such drawings:

FIG. 2 illustrates TABLES 1–3 useful for understanding the method and apparatus of FIG. 1;

FIG. 4 illustrates TABLES 4–6 useful for understanding the method and apparatus of FIG. 1;

DETAILED DESCRIPTION OF THE PREFERRED EMBODIMENT

Figure 3:
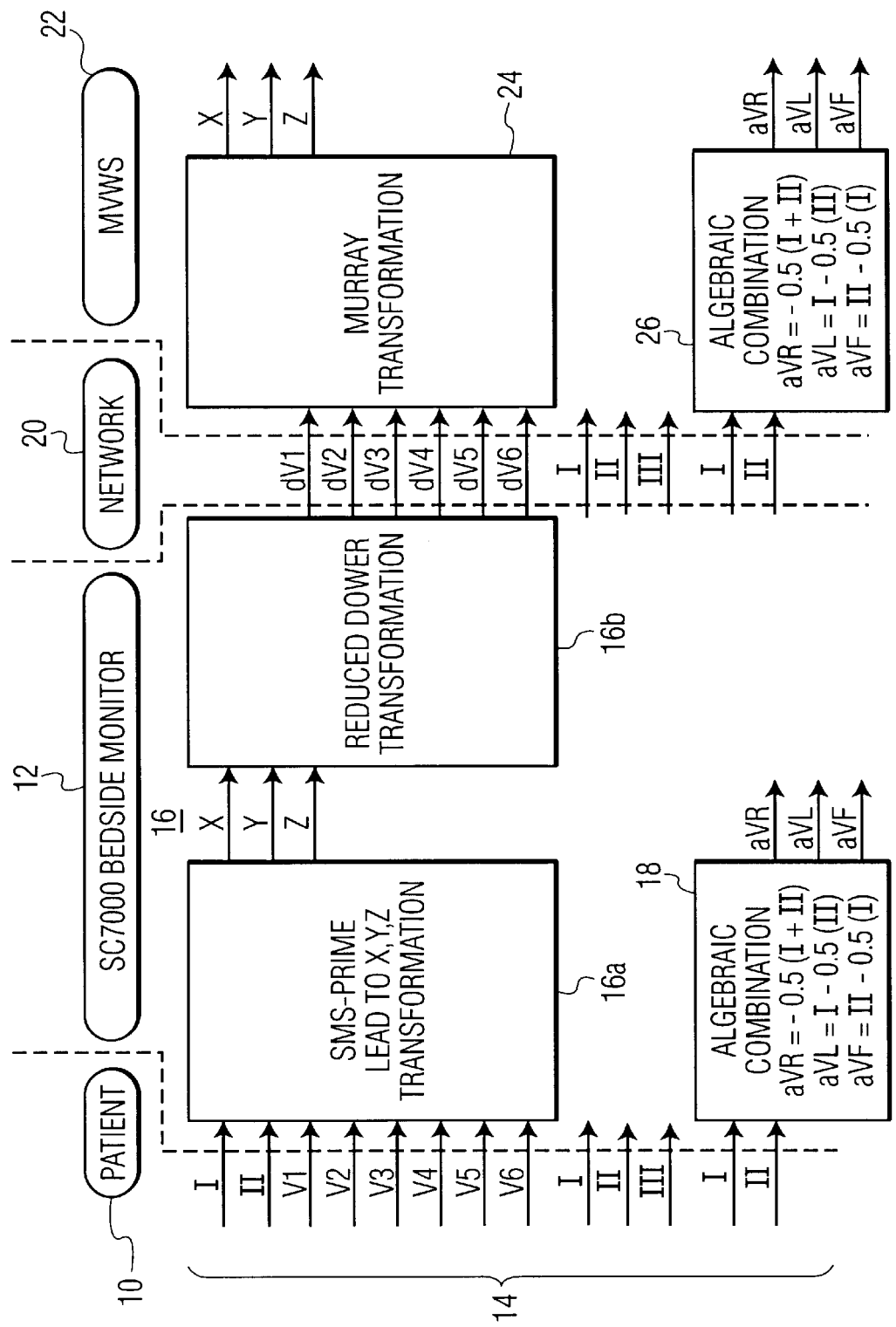
FIG. 3 illustrates the method and apparatus of the invention for Frank lead construction.

Referring to FIG. 3, Limb lead electrodes RA, LA, RL, and LL are placed on a patient 10 in the standard limb electrode positions. Chest Electrodes V1, V2, V3, V4, V5, and V6 are placed on the patient 10 in Frank electrode positions I, E, C, A, M, and H respectively. The contribution of the Frank electrode F will be computed algebraically from the formula $F=((2\times\text{lead } II)-(\text{lead } I))/3$.

A Siemens SC7000 Bedside Monitor 12 is illustrated as receiving the signals detected by the electrodes 14. A signal processor 16 inside of monitor 12 includes an SMS-Prime Lead to X, Y, Z Signal Transformation processing step 16a which processes the Prime lead electrode signals according to the following linear equations:

$X=0.610*V4+0.171*V3-0.781*V1$ (EQ 4)

$Y=0.437*II-0.218*I+0.345*V5-1.000*V6$ (EQ 5)

$Z=0.133*V4+0.736*V5-0.264*V1-0.374*V2-0.231*V3$ (EQ 6)

In FIG. 4, TABLE 4 illustrates a matrix representation for EQUATIONS 4, 5 and 6.

The X, Y, and Z signals computed using the SMS Prime Lead to X, Y, Z Transformation are themselves transformed by processing step 16b using the reduced Dower Transformation illustrated in TABLE 5 of FIG. 4. These two linear transformations combine to generate a set of derived leads in the SC 7000 bedside monitor that are made available on the network.

Figure 1:
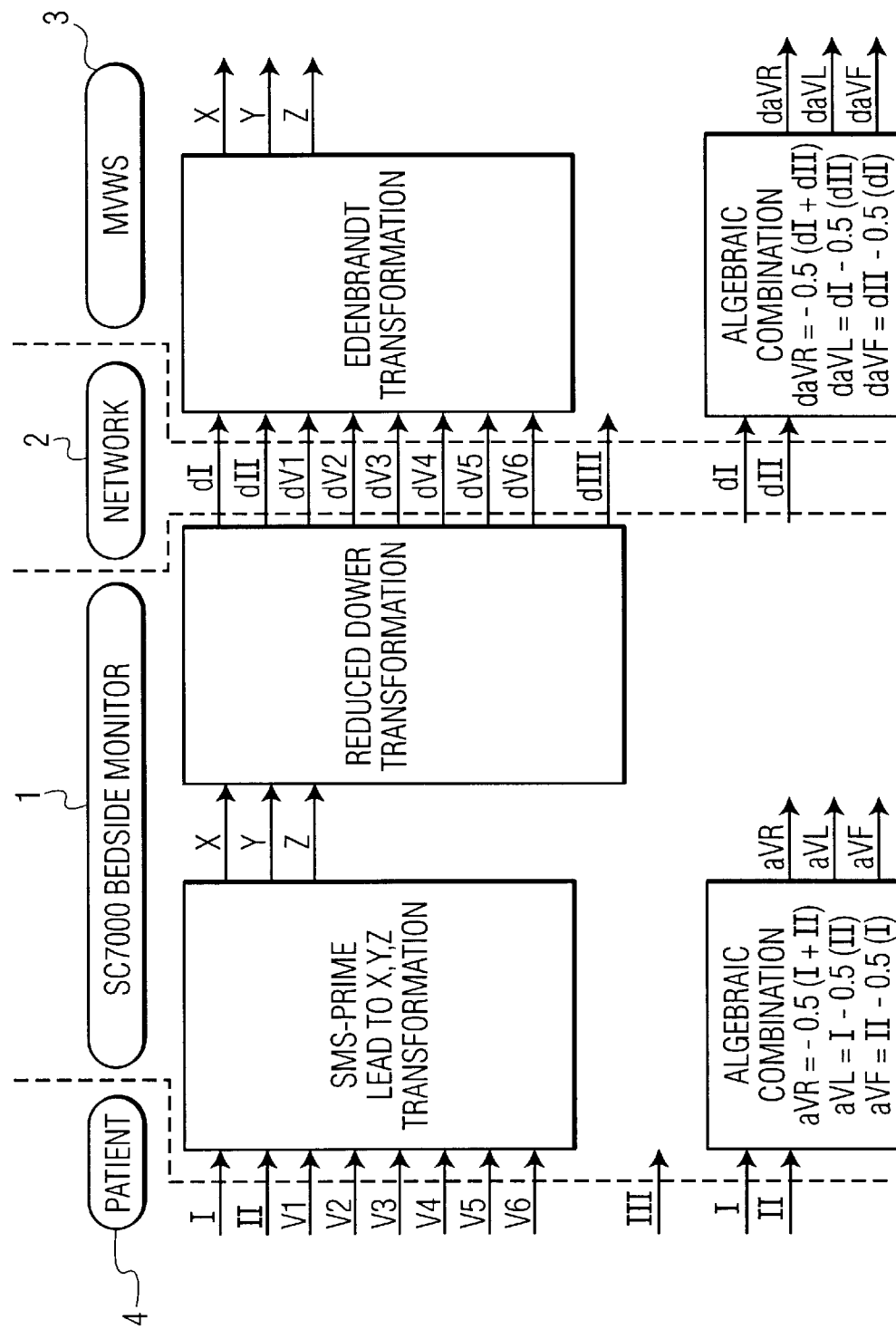
FIG. 1, previously described, illustrates a prior art method and apparatus for Frank lead construction.

However, in accordance with the principles of the present invention, the set of derived leads actually available on the network is a subset of the full complement of derived leads, and consists of derived(d) leads dV1, dV2, dV3, dV4, dV5, and dV6. Furthermore, in the present invention, sampled leads I, II, and III are made available on the network (i.e., the actual or true leads), as compared with the derived limb leads provided to the network as described in the FIG. 1 prior art. An algebraic formula is used to derive the augmented leads aVR, aVL and aVF locally on the SC7000 bedside monitor 12, using an Algebraic Combination processing step 18 as shown below:

$aVR=-0.5(I+II)$ $aVL=I-0.5\ (II)$ $aVF=II-0.5(I)$

Given that L is a 9×1 lead array representing lead values at a particular instant, $$L = \begin{bmatrix} V1 \\ V2 \\ V3 \\ V4 \\ V5 \\ V6 \\ III \\ II \\ I \end{bmatrix}$$

and that SMSPrime represents the 3×9 transformation in TABLE 4, and RDower represents the 9×3 transformation in TABLE 5, the derived lead set D(dI, dII, dIII, dV1, dV2, dV3, dV4, dV5, and dV6) can be computed as follows:

$D=R\text{Dower} \cdot SMS\text{Prime} \cdot L$

However, as shown in FIG. 3, in the present invention only the subset of the derived leads (i.e., dV1–dV6) are available on system network 20, along with the sampled limb leads I, II, and III.

A Siemens MultiView Workstation (MVWS) 22 is connected to the network. A software application within MVWS consumes 22 the set of derived leads available on the network (dV1–dV6) and reconstructs the X, Y, Z leads using the new "Murray" transformation processing step 24, represented in matrix form as TABLE 6 of FIG. 4.

Given that W is a 6×1 lead array representing derived lead values at a particular instant, $$W = \begin{bmatrix} dV1 \\ dV2 \\ dV3 \\ dV4 \\ dV5 \\ dV6 \end{bmatrix}$$

and that "Murray" represents the 3×6 transformation in TABLE 6, the derived Frank lead set F(X, Y, Z) can be computed as follows:

$$F = \text{Murray} \cdot W$$

An algebraic formula is used to derive the augmented leads aVR, aVL and aVF locally on the MVWS 22, as indicated by Algebraic Combination processing step 26 in FIG. 3. As preferred by clinicians, and in accordance with the present invention, these are actually sampled augmented leads, since the input to Algebraic Combination processing step 26 are sampled leads I and II.

Thus, there has been shown and described a novel method and apparatus for Frank lead reconstruction from derived chest leads which fulfill all the objects and advantages sought therefore. Many changes, modifications, variations, and other uses and applications of the subject invention will, however, become apparent to those skilled in the art after considering this specification and its accompanying drawings which disclose preferred embodiments thereof. For example, although electrode placement accorded to Frank positions I, E, C, A, M and H are illustrated herein, as well known by those of ordinary skill in this technology, other electrode placements are possible which still allow construction of X, Y and Z leads such as the EASI lead system as described in U.S. Pat. No. 6,052,615.

All such changes, modifications, variations and other uses and applications which do not depart from the spirit and scope of the invention are deemed to be covered by this patent.

What is claimed is:

1. An ECG signal transformation system for providing ECG lead signals comprising three Frank lead signals X, Y, and Z, comprising:
    an input processor for receiving data representing a plurality of no more than seven chest lead signals being derived from weighted linear combinations of Frank Lead signals sensed from a plurality of electrodes of a set of patient attached Frank electrodes and limb lead electrodes;
    said processor for applying coefficients of a transformation matrix to data exclusively representing said received derived chest lead signals to provide data representing three Frank lead signals X, Y, and Z; and
    said processor for providing said data representing three Frank lead signals X, Y, and Z for output.

2. The apparatus of claim 1 wherein
    said plurality of chest lead signals comprise 6 signals dV1, dV2, dV3, dV4, dV5, and dV6, said data representing said derived chest lead signals dV1, dV2, dV3, dV4, dV5 and dV6 is derived by applying a Dower transformation matrix to data representing an original set of Frank lead signals.

3. The apparatus of claim 2 wherein said transformation matrix coefficients correspond to the following values, with a 20% tolerance

|   | dV1 | dV2 | dV3 | dV4 | dV5 | dV6 |
|---|---|---|---|---|---|---|
| X | −0.407579 | −0.130520 | 0.322612 | 0.250985 | 0.123851 | 0.081250 |
| Y | 4.187331 | 0.885971 | −3.719876 | 0.079144 | 2.772391 | 2.627536 |
| Z | 0.187753 | −0.220349 | −0.612081 | −0.045136 | 0.342818 | 0.379452 |

4. The apparatus of claim 1 wherein
    said input processor also receives data representing a sampled, non-derived version of at least two of Einthoven ECG lead signals I, II and III from said limb lead signals, and
    said processor generates data representing augmented lead signals from said data representing said sampled, non-derived versions of Einthoven ECG leads I, II and III.

5. The apparatus of claim 4, wherein
    said augmented lead signals comprise at least a aVR, aVL, aVF lead signal.

6. The apparatus of claim 1 wherein
    said plurality of chest lead signals comprise 6 signals dV1, dV2, dV3, dV4, dV5 and dV6.

7. The apparatus of claim 1 wherein
    said data representing three Frank lead signals X, Y, and Z provided by said processor comprises re-constructed versions of said original set of Frank lead signals X,Y and Z.

8. A patient monitoring system comprising:
    an input processor for receiving ECG signals from a plurality of electrodes of a set of Frank electrodes and limb lead electrodes attached to a patient and for processing said received signals using weighted linear combinations of Frank Lead signals to provide data representing a plurality of derived chest lead signals;
    a data processor; and
    a communication interface for communicating, via a communication network, said data representing a plurality of derived chest lead signals to said data processor, said data processor for applying coefficients of a transformation matrix to data exclusively representing said received derived chest lead signals to provide data representing three Frank lead signals X, Y, and Z, said data processor being located remote from said input processor.

9. The system of claim 8, wherein
    said input processor receives data representing a sampled, non-derived version of at least two of Einthoven ECG lead signals I, II and III from said limb lead electrodes, and said communication interface communicates, via said communication network, said data representing sampled, non-derived version of at least two of Einthoven ECG lead signals I, II and III to said data processor for use in generating data representing conventional augmented lead signals.

10. The system of claim 9, wherein said augmented lead signals comprise at least one of aVR, aVL, aVF signals.

11. A method for transforming data representing derived chest lead signals into Frank lead signals X, Y and Z, comprising the steps of:
    storing coefficients in a transformation matrix;
    applying only data representing a plurality of chest lead signals being derived from weighted linear combinations of Frank lead signals sensed from a plurality of electrodes, adapted to be attached to a patient, in Frank electrode positions and limb lead positions to said transformation matrix; and providing output signals comprising data corresponding to application of said transformation matrix coefficients to said data representing a plurality of chest lead signals derived from linear transformations to a set of patient attached Frank electrodes and limb lead electrodes, said output signals corresponding to three Frank lead signals X, Y, and Z.

12. The method of claim 11 said transformation matrix coefficients correspond to the following values, with a 20% tolerance

|   | dV1 | dV2 | dV3 | dV4 | dV5 | dV6 |
|---|-----|-----|-----|-----|-----|-----|
| X | −0.41 | −0.13 | 0.32 | 0.25 | 0.12 | 0.08 |
| Y | 4.19 | 0.88 | −3.72 | 0.08 | 2.77 | 2.63 |
| Z | 0.19 | −0.22 | −0.61 | −0.04 | 0.34 | 0.38 |

13. An ECG signal transformation network for providing ECG lead signals comprising three Frank lead signals X, Y, and Z, comprising:

an input processor for receiving, (a) data representing a plurality of chest lead signals being derived from linear transformations of a plurality of electrodes of a set of patient attached Frank electrodes and limb lead electrodes;

(b) data representing at least two of a sampled, non-derived version of Einthoven ECG lead signals I, II and III;

said processor applying coefficients of a transformation matrix to data representing said received derived chest lead signals to provide data representing three Frank lead signals X, Y, and Z; and said processor providing said data representing three Frank lead signals X, Y, and Z and said at least two of said sampled, non-derived versions of Einthoven ECG lead signals I, II and III for output.

\* \* \* \* \*